US010729439B2

(12) United States Patent
Moustafa

(10) Patent No.: US 10,729,439 B2
(45) Date of Patent: Aug. 4, 2020

(54) MAGNETIC WOUND CLOSURE DEVICE AND METHOD OF USE

(71) Applicant: Moustafa Moustafa, Beverly Hills, CA (US)

(72) Inventor: Moustafa Moustafa, Beverly Hills, CA (US)

(*) Notice: Subject to any disclaimer, the term of this patent is extended or adjusted under 35 U.S.C. 154(b) by 284 days.

(21) Appl. No.: 15/625,703

(22) Filed: Jun. 16, 2017

(65) Prior Publication Data

US 2018/0168653 A1  Jun. 21, 2018

Related U.S. Application Data

(63) Continuation of application No. 15/381,444, filed on Dec. 16, 2016, now Pat. No. 9,693,776.

(51) Int. Cl.
*A61B 17/04* (2006.01)
*A61B 17/08* (2006.01)
*A61B 17/00* (2006.01)

(52) U.S. Cl.
CPC ............ *A61B 17/08* (2013.01); *A61B 17/085* (2013.01); *A61B 2017/00876* (2013.01); *A61B 2017/081* (2013.01)

(58) Field of Classification Search
CPC ... A61B 17/0466; A61B 17/08; A61B 17/083; A61B 17/085; A61B 17/10; A61B 17/11; A61B 17/122; A61B 2017/00867; A61B 2017/081; A61F 13/023; A61F 2210/009; A41F 1/002; A61D 2203/00; Y10T 292/11; Y10T 24/32; Y10T 24/2493
See application file for complete search history.

(56) References Cited

U.S. PATENT DOCUMENTS

| | | | |
|---|---|---|---|
| 3,102,314 A | 9/1963 | Alderfer | |
| 3,422,816 A * | 1/1969 | Palfrey | A61B 5/06 604/362 |
| 4,825,866 A | 5/1989 | Pierce | |
| 4,945,049 A * | 7/1990 | Hamaya | B03C 1/01 435/168 |
| 5,411,730 A * | 5/1995 | Kirpotin | A61K 41/0052 252/62.56 |
| 5,423,736 A | 6/1995 | Cartmell | |
| 5,478,308 A | 12/1995 | Cartmell | |
| 6,301,754 B1 * | 10/2001 | Grunberger | A41F 1/002 24/303 |
| 6,730,014 B2 | 5/2004 | Wilk | |
| 7,556,632 B2 | 7/2009 | Zadno | |
| 8,267,959 B2 | 9/2012 | Fällman | |
| 9,402,605 B2 | 10/2016 | Viola | |
| 9,486,217 B2 * | 11/2016 | Moustafa | A61B 17/085 |
| 2005/0228442 A1 | 8/2005 | Wheatley | |
| 2007/0060951 A1 | 3/2007 | Shannon | |
| 2009/0036922 A1 | 2/2009 | Riskin | |

(Continued)

*Primary Examiner* — Kathleen S Holwerda
(74) *Attorney, Agent, or Firm* — Trojan Law Offices

(57) ABSTRACT

A wound closure device using magnets to draw skin together. When two skin adhering magnets are placed on opposite sides of a wound in a polar opposite configuration, the magnets attract each other, thus drawing the skin underneath the magnets together and reapproximating wound edges. The device includes hollow tubular enclosures that enclose powdered magnetic material and permits two magnets to maintain a linear or non-linear shape along linear or non-linear edges of a wound.

7 Claims, 8 Drawing Sheets

(56) References Cited

U.S. PATENT DOCUMENTS

2010/0100022 A1    4/2010   Greener
2010/0268270 A1   10/2010   Viola
2012/0095502 A1    4/2012   Bargon
2015/0088195 A1*   3/2015   Moustafa ............. A61B 17/085
                                                                                                    606/216

* cited by examiner

MAGNETIC WOUND CLOSURE DEVICE AND METHOD OF USE

CROSS RELATED APPLICATIONS

This application is a continuation of U.S. patent application Ser. No. 15/381,444, filed Dec. 16, 2016.

FIELD OF THE INVENTION

The present invention relates generally to a device useful for wound healing, and more particularly to a magnetic device that draws wound edges in proximity to each other.

BACKGROUND OF THE INVENTION

Wounds usually occur when there is trauma to the skin and underlying tissue. Types of trauma include lacerations, abrasions, incisions, punctures, and penetrations. After trauma, the wound begins to heal in a complex series of biochemical processes occurring in several wound-healing phases. The phases of healing are often categorized into a hemostasis phase, an inflammatory phase, a proliferative phase and a remodeling phase. In hemostasis, active bleeding is controlled by clotting. In the inflammatory phase, pathogens are removed by the body away from the wounded area, and biological factors are released (which later cause the division of cells involved in the proliferative phase). In the proliferative phase, new blood vessels are formed and wound contraction occurs. Also in the proliferative phase, epithelial cells cover the wound, providing an area of growth for new tissue. During contraction, the wound is made smaller by myofibroblasts attaching to the wound edges, and finally, during the remodeling phase, collagen fibers are realigned along tension lines formed during the earlier phases of healing.

Not only is the process of wound healing complex, it is also fragile because many factors can lead to a disruption of proper wound healing, including re-injury of the tissue, bacterial infection, and physical stress on the damaged tissue. A variety of devices and methods have been used to aid in the wound healing process. These devices and methods are generally divided into one of three types: primary intention, secondary intention, and tertiary intention. The primary intention devices and methods bring the edges of the wounds together, so that the edges are reapproximated. Reapproximation helps to minimize scarring, and increases the speed at which wound contraction and healing occur. Examples of primary intention devices and methods include the use sutures, staples, tape, glue, and hooks. Primary intention techniques to heal wounds are the most common techniques used by practitioners.

While not as commonly used, secondary intention devices and methods include first allowing the wound to first granulate without closing the wound. The wound is packed and drained, often daily, to remove debris and encourage granulation tissue formation. Still less common are tertiary intension devices and methods, which delay the closure of the wound even longer, so that the practitioner can close the wound at a later time. Tissue grafting is an example of a tertiary method for wound healing.

Wound edge reapproximation is key to wound healing. If the edges of the wound are not immediately reapproximated soon after injury, healing may be delayed. This delay in healing may leads to scarring and infection. While in some circumstances a delay is advantageous, practitioners generally want to close an open wound as soon as possible.

The traditional method to reapproximate wound edges is by sutures, where a practitioner stitches a threading material to connect opposing sides of a wound. Sutures and suturing techniques are well known in the prior art, such as described by Fallman in U.S. Pat. No. 8,267,959. Other devices and methods to reapproximate wound edges include hooking devices, such as the hook closure device disclosed by Bargon in U.S. patent application Ser. No. 13/266,825, where a band placed over a wound has a multiplicity of hook elements that engage a mesh on the opposing side of a wound.

The use of adhesive strips is another method to aid in wound closure. In U.S. Pat. No. 4,825,866 to Pierce, adhesive strips are placed on opposite sides of a wound and drawn together to reapproximate the wound edges. Stapling and clipping the edges of wound are other techniques to reapproximate wound edges, as described by Zadno in U.S. Pat. No. 7,556,632.

The use of magnets to reapproximate wound edges also has been previously described. U.S. patent application Ser. No. 10/512,964 to Wheatley and U.S. Pat. No. 9,402,605 to Viola are two applications that have described tissue-joining devices comprising interconnecting components where the magnetic components are attracted to each other and draw tissue together using magnets attached to a patient's skin. Flexible magnetic devices have improved the ability to place magnets on wounds where either the wound itself is non-linear or where the wound is located on a curved surface. U.S. Pat. No. 9,486,217 to Moustafa discloses the use of flexible magnets to reapproximate wound edges that are non-linear or on a curved surface.

Other compositions and methods to reapproximate wound edges include the use of medical adhesives, such as cyanoacrylate glues that provide for very tight, high-strength closure of wounds without the need for the physical closure accomplished with sutures. However, cyanoacrylate based glues have been associated with the formation of toxic byproducts, and even non-toxic versions are generally only useful for smaller, shallow lacerations in low-tension areas. These adhesives can be very unforgiving if the practitioner needs to remove the glue. Another disadvantage of using glues for wound closure is that leakage of glues can cause serious ramifications, especially if the adhesives are toxic and the wounds are near sensitive anatomical structures, such as the eye. Still another disadvantage is that adhesives can trap pathogens and other particles within the wound.

Each type of wound closure device and technique has advantages and disadvantages. Sutures pose the risk of injury to the patient caused by the needle as well as to health care professions. The process of suturing also can take a substantial amount of time depending on the size of the wound. Using staples for wound closure is more rapid than suturing, however, unlike sutures, which may be absorbed by the body, staples usually have to be removed by a special tool. Sutures and staples also require applying local anesthesia, which could be dangerous to the patient, especially in the event of an allergic reaction. Furthermore, if the practitioner needs to enter the wound area, the sutures or staples need to be cut or removed, and both sutures and staples can lead to scarring.

Complex wound closure devices that reduce some of these disadvantages have many individual parts, are difficult to apply, or are expensive. Accordingly, it would be advantageous to make available a novel wound closure device that reduces these stated disadvantages and there remains a need for quick and easy to use devices and methods to reapproximate wound edges.

SUMMARY OF THE INVENTION

The present invention relates to a wound closure device and methods of reapproximating wound edges, which lead to improved wound healing. It is an object of the present invention to provide a magnetic wound closure device, such that when two magnets are attached to skin on opposites sides of a wound, the magnets attract each other, thereby pulling together the edges of the wound. Before the magnets reapproximate the wound edges, the magnets are separated by a partition on a peelable removable sheet so that the practitioner can place the device on the patient in a precise location before the magnets are drawn together. Once the removable sheet is removed from the magnet, the magnets draw in toward each other and pull in the skin edges around the wound. There are several advantages to the described invention, including: 1) placement of the device on a patient is faster than using staples or sutures, 2) no need to wait for an anesthetic, 3) less trauma, 4) no painful injections are needed, 5) inspection of the wound is simple because the device is easily removable, and 6) the device can be easily manufactured in a variety of sizes and shapes that accommodate various wound sizes.

The magnetic wound closure device has a first magnet and a second magnet. The first magnet and second magnet are characterized as elongated magnets each having a top surface, a bottom surface, an inner edge, and an outer edge. The inner edge of the first magnet and the inner edge of the second magnet are opposite polarities of each other. The device also includes a removable sheet having an elongated partition member. The removable sheet is designed to indirectly connect the first magnet to the second magnet by adhering to the top surface of the first magnet and top surface of the second magnet. The removable sheet has a top surface and a bottom surface. The bottom surface of the removable sheet is removably affixed to the top surfaces of the two magnets. The elongated partition member extends from the bottom surface of the removable sheet and is designed to be positioned between the inner edges of the two magnets to separate them. The elongated partition member thereby prevents the inner edge of the magnets from directly contacting each other when the wound closure device is being placed along the edges of a wound. When the removable sheet and elongated partition member are removed from the magnets, the magnets are magnetically drawn to each other, causing the inner edges of each magnet to move together, thereby reapproximating wound edges.

Another embodiment of the invention is where the bottom surfaces of the magnets have an adhesive layer to affix the magnets to the skin of a patient. The adhesive layer may be covered be an adhesive covering before being removed and placed on a patient. The removable sheet may be peelable and also have an adhesive layer on its bottom surface for affixing the removable sheet to the first and second magnet.

Another embodiment of the invention is where the magnets include a protective covering, such as a polymer enclosure.

In a further embodiment of the invention, the bottom surface of the removable sheet is sized and shaped substantially the same as the top surfaces of the magnets when the magnets are aligned together along their respective inner surfaces. The elongated partition member is positioned substantially along the middle of the longitudinal axis of the removable sheet.

In another embodiment of the invention, the wound closure device includes a first magnet and a second magnet. The magnets are elongated magnets, each having a top surface, a bottom surface, and inner edge and an outer edge. The inner edge of the first magnet has an opposite polarity to the inner edge of the second magnet. To prevent the inner edges of the magnets from shifting along the longitudinal axis, each inner edge has a plurality of notches and protrusions. The notches on each inner edge are complementary shaped to protrusions on the opposing magnet, so that when the inner edges of each magnet are aligned with each other, the complementary notches and protrusions reduce the possibility of movement of the magnets along their respective inner edges. When the magnets are in proximity to each other, the inner edges move toward each other, thereby drawing the skin under the magnets to each other and reapproximating wound edges.

In another embodiment, the plurality of notches and protrusions are serrations, and the serrations can be V-shaped serrations.

In still another embodiment, the wound closure device having notched inner edges may be combined with the removable sheet having an elongated partition member to aid in placement of the device on the patient.

Another object of the invention to provide a method of reapproximating wound edges. The steps involve: adhering the first magnet and the second magnet substantially near edges of a wound of a patient, and removing the removable sheet that has the elongated partition member separating the first and second magnet. The inner edge of the first wound closure device and the inner edge of the second wound closure device attract each and reapproximate wound edges.

In another embodiment of the invention, the magnetic wound closure device is made of a first magnet and a second magnet. The first magnet has a first flexible enclosure and the second magnet has a second flexible enclosure. Each enclosure is filled with a powdered magnetic material. The magnetic powder within the enclosures allow the magnets to maintain either a linear or non-linear shape even after they are placed on the patient. The place of the first and the second magnet on opposing edges of a non-linear wound allow the magnets to attract each other along a non-linear inner edge of the first magnet and a non-linear edge of the second magnet, thereby reapproximating wound edges of a non-linear wound.

BRIEF DESCRIPTION OF THE DRAWINGS

These and other features and advantages of the present invention will become appreciated, as the same becomes better understood with reference to the specification, claims and drawings herein:

DETAILED DESCRIPTION OF THE INVENTION

Figure 1:
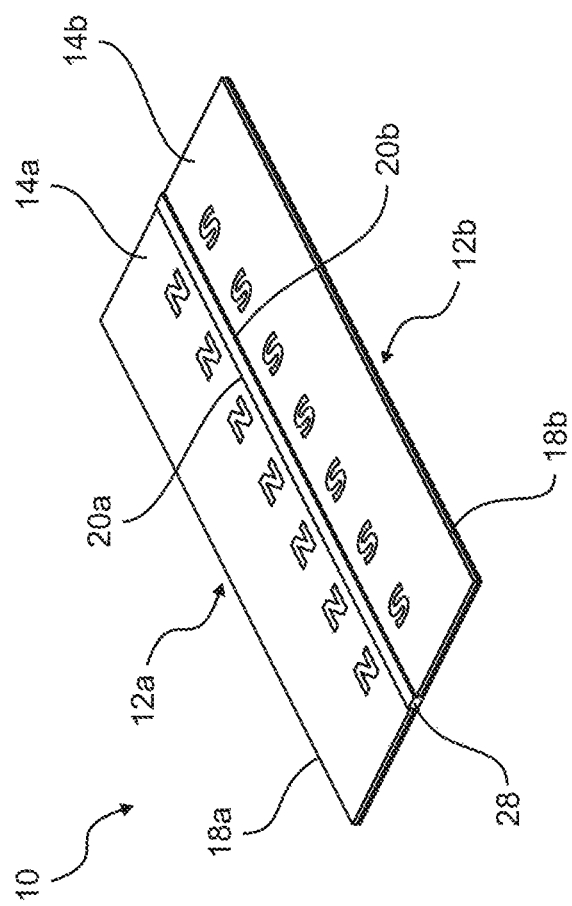
FIG. 1 is a bottom perspective view of an embodiment of a wound closure device.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

It will be understood that when an element is referred to as being "on" another element, it can be directly on the other element or intervening elements may be present there between. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section.

As used herein, the singular forms "a," "an," and "the," are intended to include the plural forms as well, unless the context clearly indicates otherwise. It will be further understood that the terms "comprises" and/or "comprising," "includes" and/or "including," and "have" and/or "having," when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom," and "upper" or "top," and "inner" or "outer," may be used herein to describe one element's relationship to another element as illustrated in the Figures. It will be understood that relative terms are intended to encompass different orientations of the device in addition to the orientation depicted in the Figures.

Unless otherwise defined, all terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing.

A wound closure device is provided for closing wounds without sutures. FIGS. 1-4 depict one embodiment of a wound closure device 10 and how the device 10 is used on a patient. The wound closure device 10 includes a first magnet 12a and a second magnet 12b. The magnets 12a, 12b are flexible elongated strips capable of flexing along the longitudinal axis, such as shown in FIG. 3. Each magnet has a top surface 24a, 24b, a bottom surface 14a, 14b, an outer edge 18a, 18b, and an inner edge 20a, 20b. The inner edges 20a, 20b have opposite magnetic polarity. For example, if the inner edge 20a of the first magnet 12a is north, then the inner edge of 20b of the second magnet 12b is south, and vice versa.

Attached to the magnets 12a, 12b is a removable sheet 26 having a top surface 27 and bottom surface 22. The removable sheet 26 can be made of any flexible material, including polymers, polyvinyls, elastomers, thermoplastics, polyolefins, polyesters, or the like. The removable sheet indirectly connects the first magnet 12a to the second magnet 12b by adhering the top surfaces 24a, 24b of the first and second magnets 12a, 12b to the bottom surface 22 of the removable sheet 26. The bottom surface 22 of the removable sheet 20 is removably affixed to the top surfaces 24a, 24b of the magnets 12a, 12b.

Extending from the bottom surface 22 of the removable sheet 26 is an elongated partition member 28. The partition member 28 may be made of the same material as the removable sheet 26 and may be integral with the sheet 26 or attached to the sheet 26. The elongated partition member 28 runs substantially down the longitudinal axis of the removable sheet 20 and is designed to be positioned between and separate the two magnets 12a, 12b along their inner edges 20a, 20b. By having the partition member 28 between the inner edges 20a, 20b, the partition member 28 prevents the inner edge 20a of the first magnet 12a from directly contacting the inner edge 20b of the second magnet 12b. This configuration allows the practitioner to maneuver the device around the wound 13 when the magnets are not yet connected directly to each other so that the first magnet 12a can be positioned on one side of the wound 13 and the second magnet 12b can be positioned on the opposing side of wound 13, with the wound 13 positioned between the two magnets 12a, 12b.

The elongated partition member 28 may have a variety of structures and in on embodiment is an elongated tab having a width of less than 2 cm, a depth of less than 2 cm. The wider the partition member 28 is, then the larger the wound 13 that can be fit between the magnets 12a, 12b. However, if the partition member 28 is too wide, the magnets will be two far apart to attract each other once the partition member 28 is removed. If the partition member 28 is too thin, then the magnets 12a, 12b would be placed directly on top of the wound and not on adjacent skin. In one embodiment, the depth of the partition member 28 is substantially the same as the depth of each magnet 12a, 12b, so that the bottom of the partition member 28 is flush with the bottom surfaces of each magnet 12a, 12b when the removable sheet 26 and magnets 12a, 12b are connected together. In other embodiments, the width and depth of the elongated partition member 28 is less than 1 cm.

Figure 2:
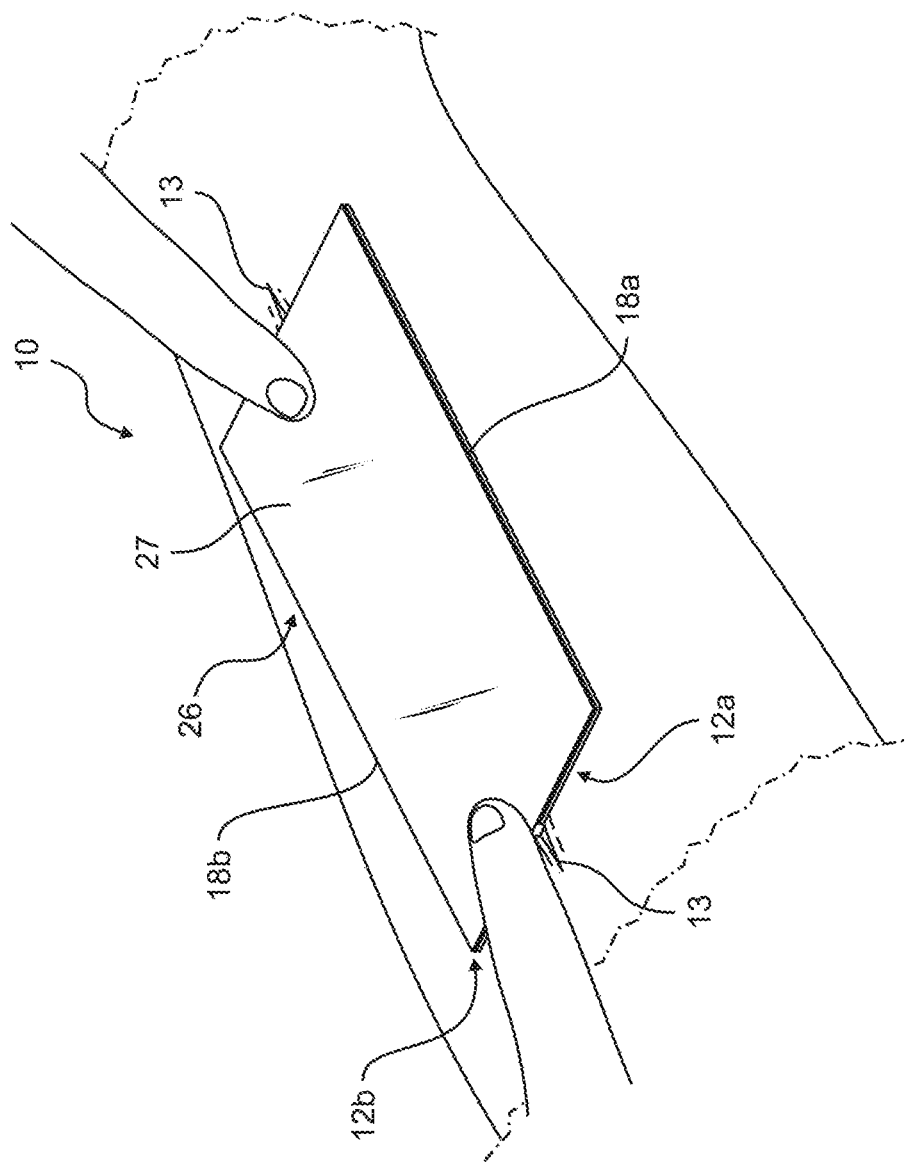
FIG. 2 is a top perspective exemplary view of the embodiment of FIG. 1 placed on an arm.
Figure 3:
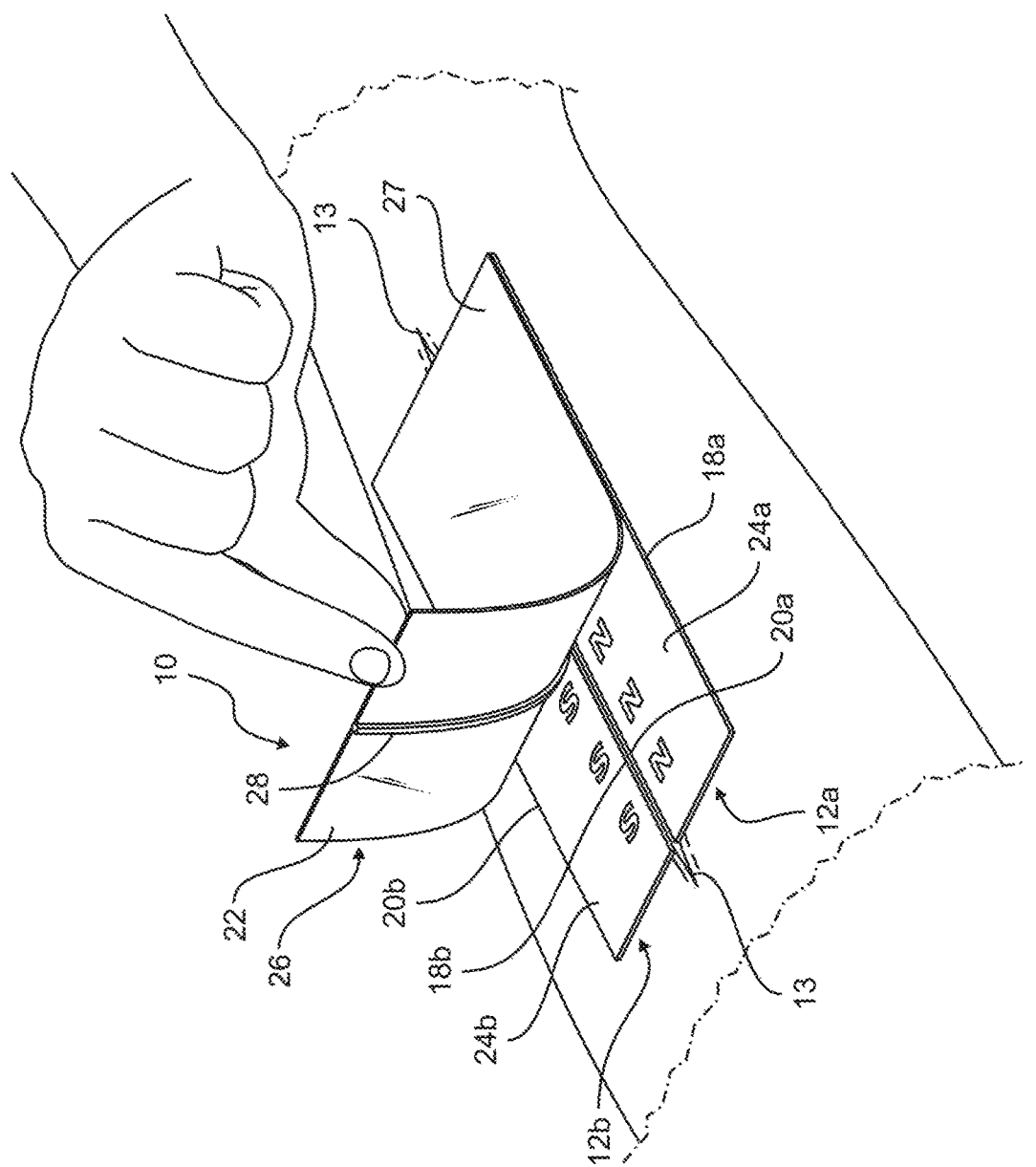
FIG. 3 a top perspective exemplary view of the embodiment of FIG. 1 as the removable layer is being peeled off and magnets still separated.
Figure 4:
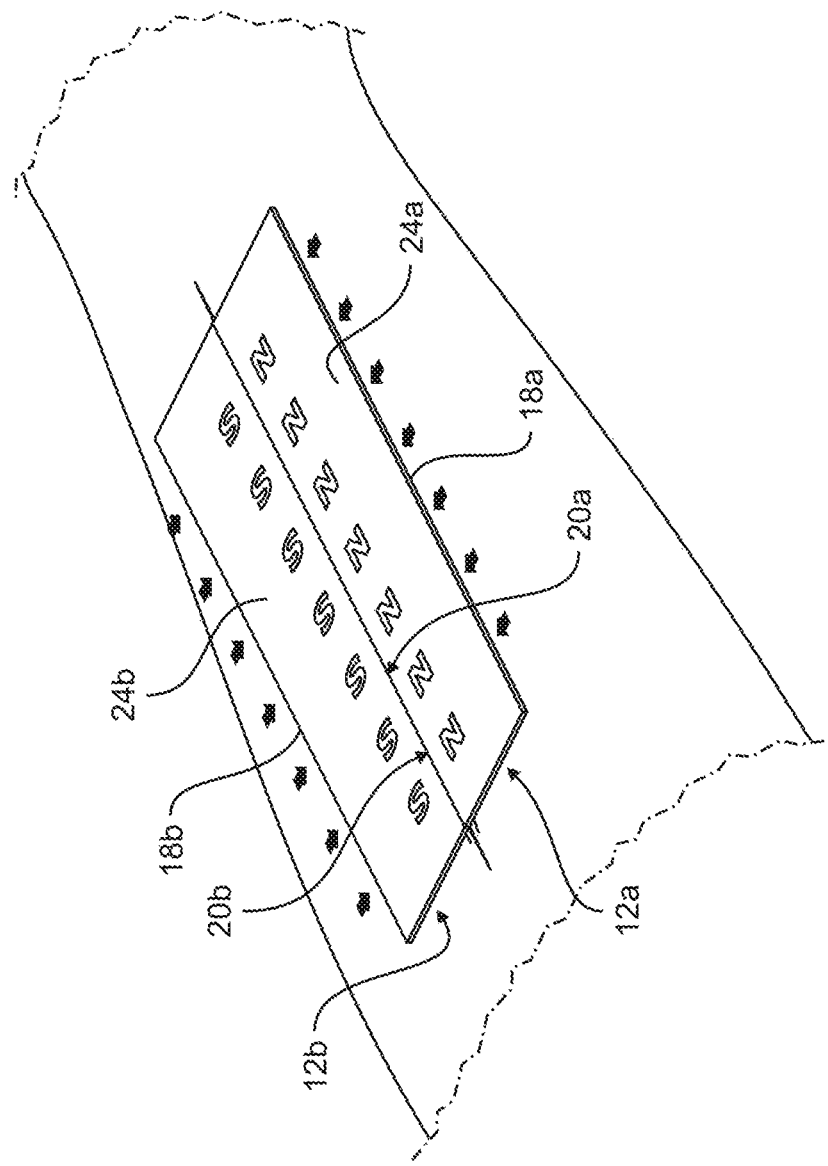
FIG. 4 is a top perspective exemplary view of the embodiment of FIG. 1 after the removable layer has been completely removed and the inner edges of the magnets have reapproximated the wound edges.

Once the device 10 is placed over the wound 13, as shown in FIG. 2, the practitioner removes the removable sheet 26, as shown in FIG. 3, by peeling the removable sheet 20 off of the magnets 12a, 12b. In FIG. 3, the magnets are still spaced apart from each other because the partition member 28 is still positioned between the magnets 12a, 12b. When the sheet 20 and partition member 28 are peeled away from the magnets 12a, 12b, the inner edges 20a, 20b of the magnets 12a, 12b are drawn together, thereby reapproximating wound edges by pulling the skin underneath the magnets 12a, 12b together.

To aid in adhering the magnets to the skin, the bottom surfaces of the magnets 14a, 14b may have an adhesive layer. The adhesive layer can be covered with a peelable cover (not shown) designed to be removed before affixing the magnets 12a, 12b to the skin. The removable sheet 26 may also have an adhesive layer, or the top surfaces of the magnets 24a, 24b may have an adhesive layer to affix the removable sheet 26 to the magnets 20a, 20b. The adhesive layer is a weak adhesive layer, which keeps the sheet 26 affixed to the magnets, but allows the sheet 26 to be easily peeled away from the magnets once the device 10 is placed on the patient. In an alternative manner to apply the device to the patient's skin, instead of an adhesive layer on the magnet, a practitioner could apply an adhesive directly on the patient's skin around a wound, and thereafter place the device on the skin adhesive.

Figure 5:
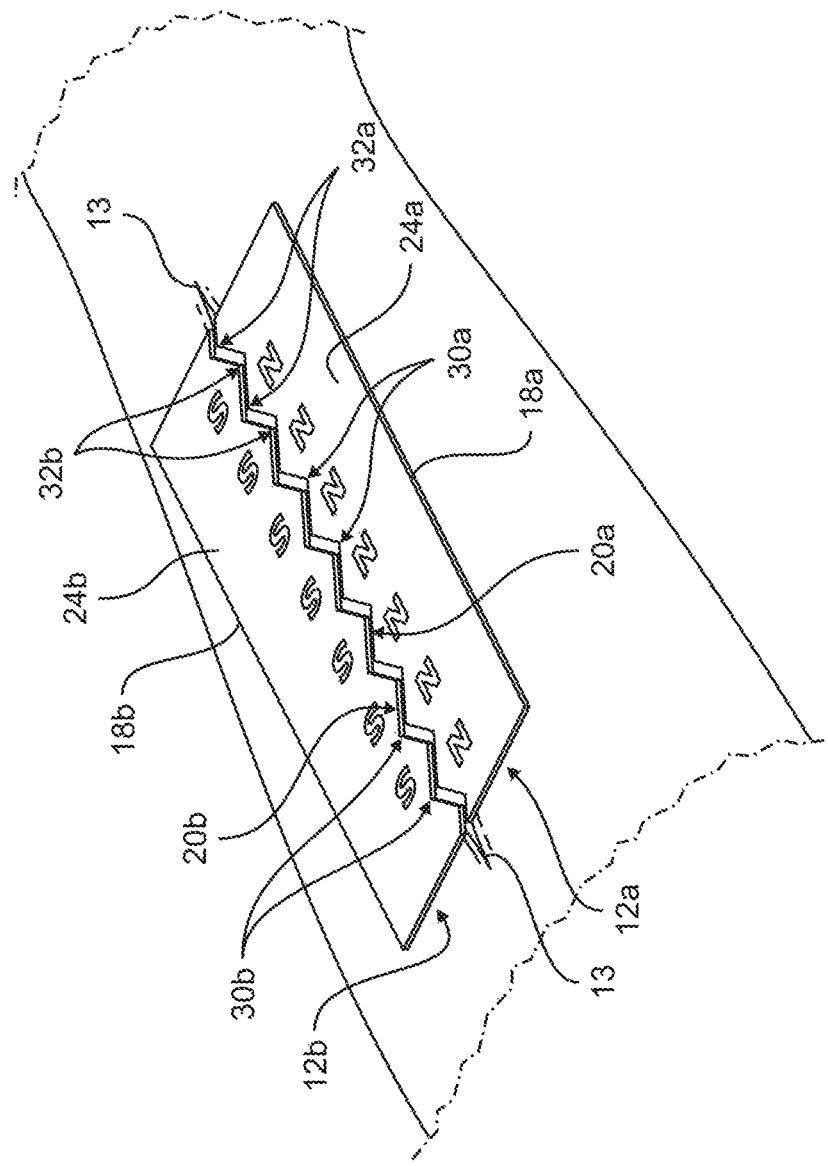
FIG. 5 is a perspective view of a wound closure device having notched and protruding inner edges along two separated magnets.
Figure 6:
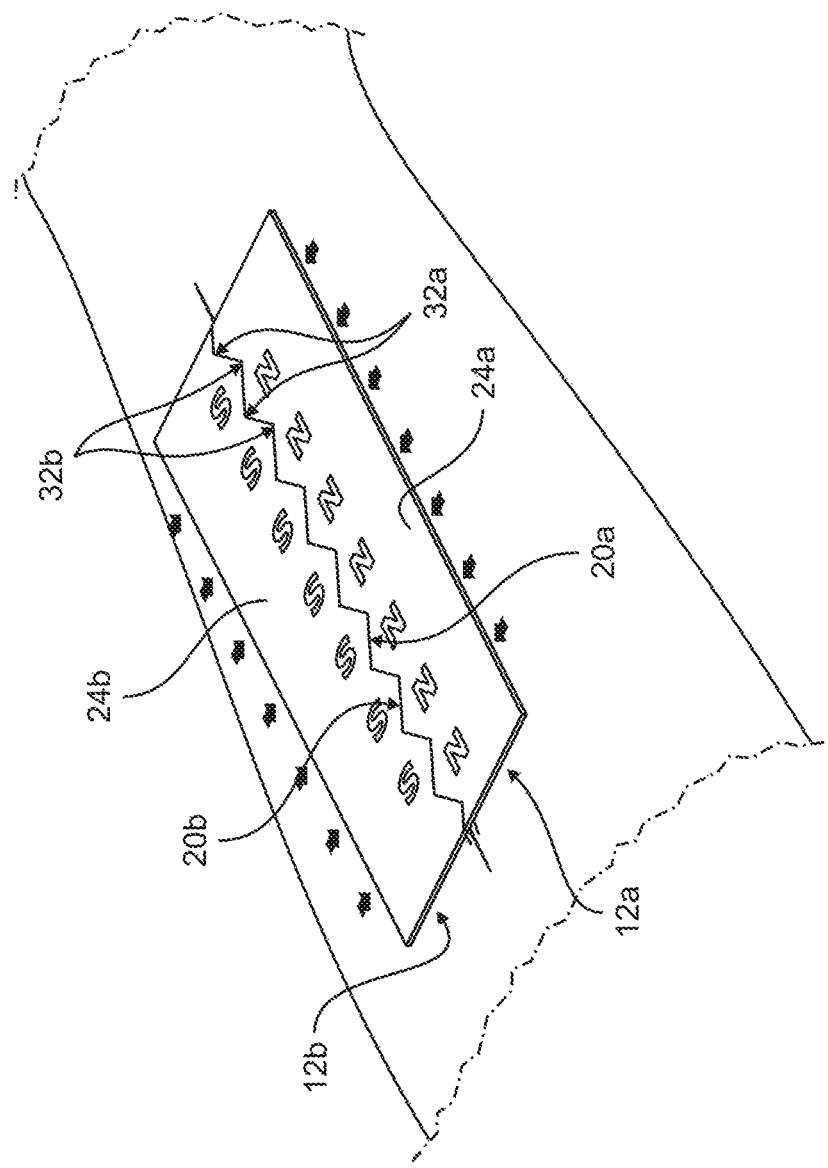
FIG. 6 is a perspective view of the wound closure device of FIG. 5 where the inner edges along the two magnets have been magnetically attracted to each other and connected.

Turning to FIG. 5 and FIG. 6, in another embodiment of the device 10, the inner edge of the first magnet 12a is characterized has having a first plurality of notches 30a and the inner edge of the second magnet 12b is characterized as having a second plurality of notches 30b. The notches 30a, 30b can be any size or shape, but are complementary shaped so that the protrusions 32a formed by the notches 30a on the first magnet 12a fit within the notches 30b of the second magnet 12b, and vice versa. When the device 10 is placed on opposite sides of the wound 13, the magnets 12a, 12b are spaced apart, as shown in FIG. 5. After placement on opposite sides of a wound, the magnets 12a, 12b attract each other so that the notches 30a, 30b interlock with the protrusions 32a, 32b on the opposing magnet, as shown in FIG. 6. As shown in FIG. 5 and FIG. 6, the notches are V-shaped, but other shapes can be imagined without detracting from the spirit of the invention, such as square shaped, rectangular shaped, circular shaped, irregularly shaped, or any other shape where a complementary protrusion can fit within the notch of an opposing magnet.

The notches 30a, 30b are advantageous because they prevent slippage and movement along the longitudinal axis of the inner edges due to the flanking effect of the arms of the notches and protrusions. Wound edge alignment is a desirable feature of wound closure because if the wound's edges are not perfectly aligned, the resulting healed wound may have a "dog ear" deformity, which would require surgical correction. The anti-slippage feature created by the notches and protrusions along the inner edges of the magnet prevents the skin from sliding underneath the magnets. Protrusions and notches can vary in size. In one embodiment, a protrusion tip is approximately 4 mm in height. In one embodiment, the length from protrusion tip to the adjacent protrusion tip is approximately 8 mm. In one embodiment, the length of the magnet is approximately 8 cm. In one embodiment, the thickness of the magnet is approximately 1 mm and the width of each magnet, from the tip of a protrusion to the outer edge 18a, 18b, is approximately 2 cm. Differences in dimensions of notches and protrusions can be well tolerated such as notches and protrusions that are at least half or at least double the notch and protrusion disclosed above.

The dimensions of each magnet 12a, 12b of device 10 can be of any length, but preferable between 3 cm and 10 cm in length, and 2 cm and 6 cm in width. Preferably, the height of each magnet 12a, 12b is between 0.5 mm and 5 mm, and approximately 1 mm in height.

In another embodiment, each magnet 12a, 12b is between 5 cm and 20 cm in length, between 1 cm and 6 cm in width, and between 0.5 mm and 10 mm in height. In another embodiment, the dimension of each magnet 12a, 12b is approximately 4 cm in length, 2 cm in width, and 1 mm in height.

Preferably, the magnets have a protective covering or are enclosed within a housing, such as a polymer enclosure. Enclosures for magnets in wound healing devices have been disclosed in other wound healing devices, as well as additional layers within the enclosure to aid in healing, such as: insulation layers, absorbent layers, polymer layers, holes that allow for drainage of fluids, adhesive layers, and removable covers, which are described and illustrated in FIG. 1 and FIG. 2 of U.S. Pat. No. 9,486,217 to Moustafa, which is fully incorporated herein by reference in its entirety.

The enclosure may be made of any one of number of polymers, but in a preferred embodiment is a silicone enclosure. Other materials for an enclosure may be made from natural or synthetic polymers including rubber, neoprene, polyvinyl chloride, polyvinyl butyral, polystyrene, polyethylene, polypropylene, nylon, polyacrylonitrile.

The magnets 12a, 12b may be made from a number of materials, such as ferromagnetic materials, or rare-earth elements, such as magnets made from alloys of neodymium, iron and boron. The advantage of rare-earth magnets, such as neodymium magnets is that their crystalline structures have very high magnetic anisotropy and can retain high magnetic moments in the solid state.

In a preferred embodiment, the magnet is a flexible magnet that is rolled or extruded in a magnetic film, and then cut to size into a magnetic sheet or strip. In one magnet useful for wound closure, the magnet comprises NdFeB magnetic powder, chlorinated polyethylene (CPE), and an annexing agent such as soybean oil.

In another embodiment, the magnet in the device is comprised of approximately 90.5% NdFeB powder, 8.5% CPE, and 1% annexing agent. In yet another embodiment, NdFeB powder may be comprised of approximately 31.0-31.8% PrNd, approximately 64-66.5% Fe, approximately 1.00-1.03% B, approximately 1.5-1.8% Dy, approximately 0.5-0.8% Co, approximately 0-0.25% Nb, and approximately 0.0-0.2% Al. Deviations from the percentages above that also allow for a strong but flexible magnet are allowed and known by persons having ordinary skill in the art.

The adhesive used in the embodiments may be made from any one of a number of adhesive compositions, including: reusable adhesives, pressure sensitive adhesives, contact adhesives, resins, epoxies, polyurethane, cyanoacrylate (CA), polymers, acrylic-based adhesives that cure under ultraviolet (UV) light, silicone based adhesives, and polyolefinic polymers. A removable cover that protects the adhesive from the environment before use may be a peel-off tape. The practitioner removes the adhesive cover before placing the device 10 on the patient's skin.

The inclusion of plasticizers within the polymer composition of the enclosure lowers the glass transition temperature ($T_g$) of the polymer, therefore allowing device 10 to flex when the magnets 12a, 12b within the polymer enclosure flexes. Plasticizers are commonly known and used in the art, and may include phthalate ester plasticizers commonly used in medical devices such as: dicarboxylic/triboxylic ester-based plasticizers, including Bis (2-ethylhexyl) phthalate, Di-n-butyl phthalate, or Diisooctyl phthalate.

Since no sutures or staples are used when applying the device 10, the invention is advantageous for emergency situations when medical personnel are overloaded, or even in non-emergency situations for use with young children who would be more apprehensive regarding traditional wound closure devices and methods.

Figure 7:
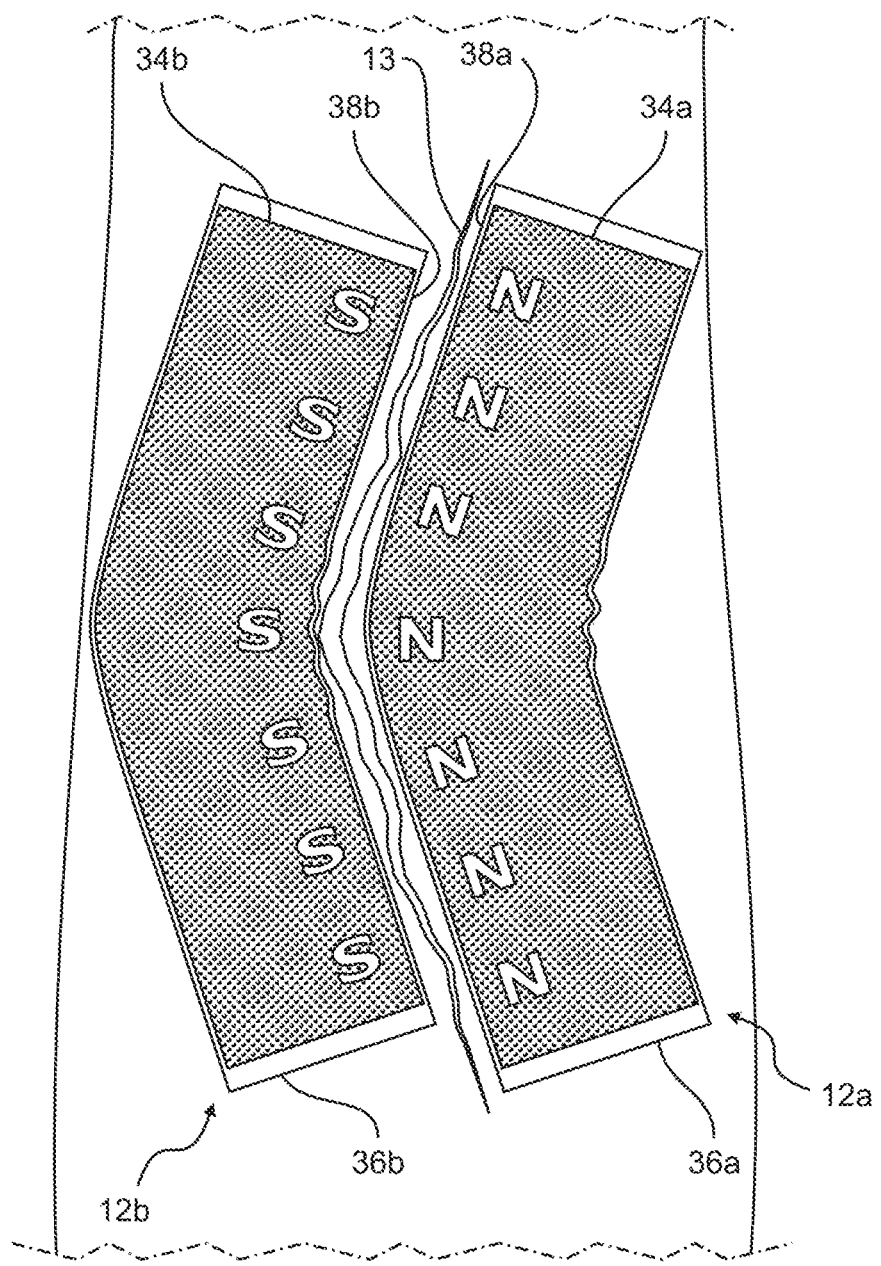
FIG. 7 is a top exemplary view of an embodiment where the wound closure device is made of two flexible tubes of powdered magnet material to easily curve around non-linear wound edges before the magnets attract together.
Figure 8:
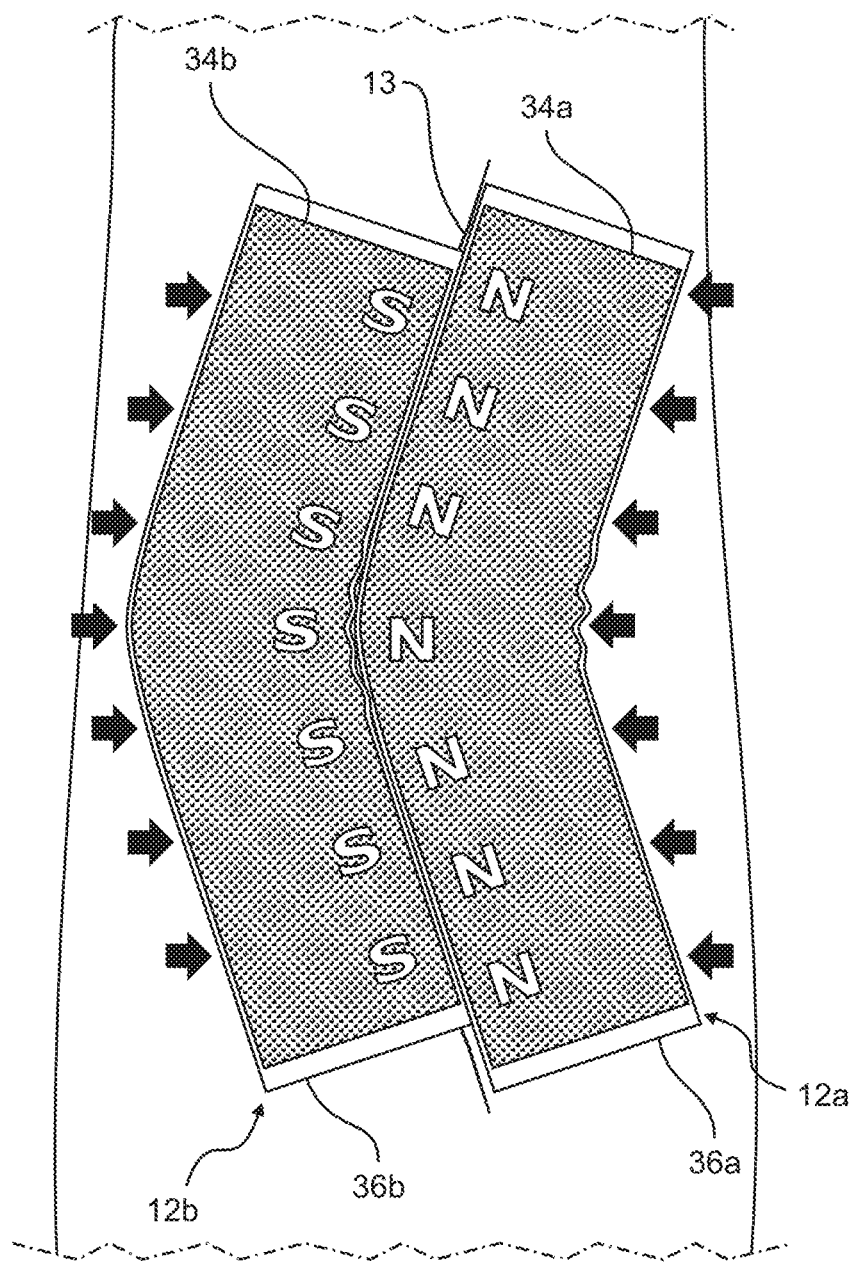
FIG. 8 is a top exemplary view of FIG. 7 after the magnets have attracted together to close the wound.

FIG. 7 and FIG. 8 illustrate another embodiment of the invention, where the magnets 12a, 12b placed on opposite edges of a wound 13 are not magnetic strips but instead or are comprised of magnetic powdered material 34a, 34b within a flexible enclosure 36a, 36b. The flexible enclosures 36a, 36b can be made of any thin, flexible material, such as plastic, polyethylene, latex, nitrile, or the like, and allow the magnets 12a, 12b to be easily positioned on a patient to match the shape of the wound. The powder 34a, 34b allows the magnets 12a, 12b to maintain either a linear shape or non-linear shape after placement on a patient. In FIG. 7 and FIG. 8, the magnets 12a, 12b are in a non-linear shape. Other types of flexible enclosures for magnetic powder may be envisioned without detracting from the spirit of the invention. In one embodiment, the flexible enclosures 36a, 36b are hollow cylindrical tubular structures, but the shapes and sizes of the flexible enclosures 36a, 36b may vary without departing from the spirit of the invention.

Examples of magnetic powder 34a, 34a that can fill the enclosures 36a, 36b can be, but are not limited to: iron oxide, barium ferrite, strontium ferrite, magnetite, Iron (II,III) oxide, neodymium powder, rare earth magnet powder, or any other permanent magnet that can be powderized and placed within the flexible enclosures 36a, 36b. FIG. 7 depicts the magnets 12a, 12b around the edges a non-linear wound before the magnets have attracted each other to reapproximate wound edges. Since the magnets 12a, 12b are comprised of magnetic powder 34a, 34b, the magnets 12a, 12b can be easily bent or curved and maintain their shapes. FIG. 8 depicts the magnets 12a, 12b of FIG. 7 after the inner edges 38a, 38b of the magnets 12a, 12b have attracted to each other, thereby reapproximating wound edges. The inner edges 38a, 38b of the magnets 12a, 12b in FIGS. 7 and 8 are shown as non-linear inner edges 38a, 38, but can also be shaped to be straight linear inner edges to approximate linear wounds as well.

The magnets illustrated in FIGS. 7 and 8 may have the same additional layers of adhesives, covers, and flexible sheets as described in the previous embodiments.

While the invention has been described in terms of exemplary embodiments, it is to be understood that the words that have been used are words of description and not of limitation. As is understood by persons of ordinary skill in the art, a variety of modifications can be made without departing from the scope of the invention defined by the following claims, which should be given their fullest, fair scope.

I claim:

1. A magnetic wound closure device for application to a wound having contours which are linear or non-linear, the improvement comprising:
    a first enclosure and a second enclosure, said first enclosure containing particles of magnetic material of a size to permit said first enclosure to be flexible, said second enclosure containing particles of material capable of being attracted to said magnetic material in said first enclosure, said particles in said second enclosure of a size to permit said second enclosure to be flexible, wherein said first enclosure and said second enclosure each have a first end and a second end;
    adhesive material secured to a surface of said first enclosure and to a surface of said second enclosure, said adhesive material capable of securing said first and second enclosures on opposing sides of said wound and along said contours of said wound;
    a partition member for positioning between said first and second enclosures, said partition member composed of material capable of preventing magnetic attraction between said materials in said first and said second enclosures, wherein said partition member extends from said first end to said second end of at least one of said enclosures; and
    whereby removal of said partition member allows said materials in said first enclosure and said second enclosure to be magnetically drawn together, thereby reapproximating said wound.

2. The magnetic wound closure device of claim 1 comprising:
    said partition member removably secured to one of said enclosures.

3. The magnetic wound closure device of claim 1 comprising:
    said partition member including a sheet to assist in the positioning and removal of said partition member.

4. The magnetic wound closure device of claim 1, wherein said magnetic material is iron oxide.

5. The magnetic wound closure device of claim 1, wherein said first enclosure and said second enclosure are made of flexible plastic.

6. The magnetic closure device of claim 1, wherein the distance between said first end and said second end of each of said first enclosure and said second enclosure is between 3 cm and 10 cm, and the width of each of said first enclosure and said second enclosure is between 2 cm and 6 cm.

7. The magnetic closure device of claim 1, wherein the distance between said first end and said second end of the first enclosure and the second enclosure are each between 5 cm and 20 cm, and the widths of the first enclosure and the second enclosure are each between 1 cm and 6 cm.

* * * * *